United States Patent [19]
Darsow et al.

[11] Patent Number: 6,031,140
[45] Date of Patent: Feb. 29, 2000

[54] PROCESS FOR PRODUCING ISOCAMPHYL CYCLOHEXANOLES

[75] Inventors: Gerhard Darsow; Wilfried Niemeier, both of Krefeld, Germany

[73] Assignee: Bayer Aktiengesellschaft, Leverkusen, Germany

[21] Appl. No.: 09/194,635

[22] PCT Filed: Jun. 3, 1997

[86] PCT No.: PCT/EP97/02870

§ 371 Date: Nov. 30, 1998

§ 102(e) Date: Nov. 30, 1998

[87] PCT Pub. No.: WO97/46505

PCT Pub. Date: Dec. 11, 1997

[30] Foreign Application Priority Data

Jun. 3, 1996 [DE] Germany ............ 196 22 187

[51] Int. Cl.[7] .................................. C07C 35/08
[52] U.S. Cl. ...................................... 568/832
[58] Field of Search .............................. 568/832

[56] References Cited

U.S. PATENT DOCUMENTS 4,014,944 3/1977 Hall et al. .................. 260/631.5
4,245,124 1/1981 Bauer et al. .................. 568/633

OTHER PUBLICATIONS

Chem Abstract, vol. 51, No. 21, Nov. 10, 1957, Abstract No. 17107CL.A. Kheïfits.

*Primary Examiner*—Michael L. Shippen
*Attorney, Agent, or Firm*—Joseph C. Gil; Noland J. Cheung

[57] ABSTRACT

A continuous process for preparing isocamphyl-cyclohexanols from isocamphy-guaiacol or isocamphyl-phenol compounds by hydrogenating one of said compounds with hydrogen at elevated temperature and elevated pressure, comprising the use of support-free molded bodies which serve as catalysts and which are obtainable by reduction of molded bodies made of compressed powders of cobalt, manganese and copper (hydr)oxides and optionally of (hydr)oxides of the alkaline earth metals are used.

16 Claims, No Drawings

PROCESS FOR PRODUCING ISOCAMPHYL CYCLOHEXANOLES

FIELD OF THE INVENTION

The invention relates to a continuous process for preparing isocamphyl-cyclohexanols from isocamphyl-guaiacol or isocamphyl-phenol by hydrogenation with hydrogen at elevated temperature and elevated pressure using support-free reduced molded bodies made of compressed powders of cobalt, manganese and copper (hydr)oxides and, optionally, of (hydr)oxides of alkaline earth metals.

BACKGROUND OF THE INVENTION

Isocamphyl-cyclohexanols are constituents of the industrially produced sandalwood perfumes, which are composed of synthetic mixtures of various terpenecyclohexanol isomers. Industrial sandalwood perfumes replace natural sandalwood oil in soaps, cosmetic products and perfume compounds.

As starting compounds for the isocamphyl-cyclohexanols, for example, the isocamphyl-guaiacols can be prepared in a known manner by reacting camphene with guaiacol with the aid of acidic catalysts, for example borontrifluoride and acetic acid; the isocamphyl-guaiacols are then converted into the isocamphyl-cyclohexanols by hydrogenation of the aromatic nucleus and cleavage of the methoxy group.

The reactions proceed according to the following equation:

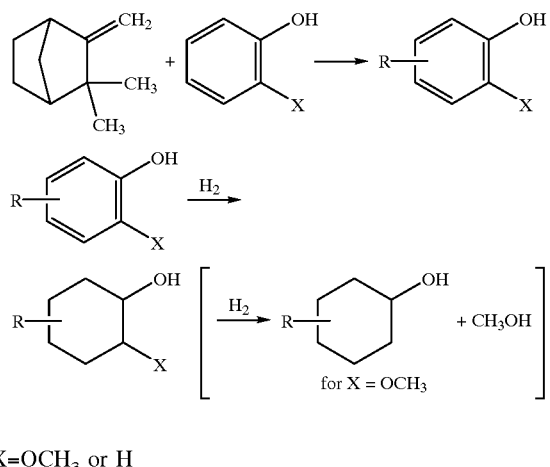

$X = OCH_3$ or $H$

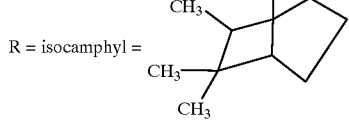

It is already known to hydrogenate alkylation mixtures of camphene and catechol (US 4 014 944) or camphene and guaiacol (DE-A 2 921 139) with hydrogen over Raney nickel to form the desired isocamphyl-cyclohexanols.

Without exception, these processes of the prior art proceed discontinuously using powdered catalysts by the suspension process.

In the case of powdered catalysts, the following difficulties exist: (1) to activate said catalysts in a controlled and uniform manner, (2) to circulate powdered catalysts with the aid of special sludge pumps and (3) to separate powdered catalysts from the reaction product quantitatively. Sludge pumps are, after all, subject to a high mechanical loading. The quantitative removal of powdered catalysts is furthermore expensive because it requires a coarse filtration and a fine filtration using equipment with switching facility. Furthermore, there is a great risk that the catalysts quickly lose their activity as a result of these additional operations and therefore furthermore cause high catalyst consumptions. In addition, powdered catalysts can only be loaded to a limited extent and can be freed from the reaction products only with difficulty, which makes their working-up difficult.

There was therefore the requirement to prepare highly loadable, acid-resistant and long-life catalysts for preparing isocamphyl-cyclohexanols, which catalysts should be free of complicated support systems and therefore capable of being worked up again.

SUMMARY OF THE INVENTION

Surprisingly, the problem described can be solved with the aid of support-free fixed-bed catalysts which can be obtained by reduction of molded bodies made of compressed metal (hydr)oxide powders.

The invention consequently relates to a continuous process for preparing isocamphyl-cyclohexanols from compounds which have the carbon skeleton of the isocamphyl-guaiacols or isocamphyl-phenols by hydrogenation with hydrogen at elevated temperature and elevated pressure, which process comprises using as catalysts support-free molded bodies which are obtainable by reduction of molded bodies made of compressed powders of cobalt, manganese and copper (hydr)oxides and optionally one or more (hydr)oxides of the alkaline earth metals.

For the catalysts to be used according to the invention, the Co proportions should be 40 to 65% by weight, the Mn proportions 10 to 20% by weight, the Cu proportions 0.1 to 0.5% by weight and, optionally, the alkaline earth metal proportions (with a plurality in the total) 0.2 to 5% by weight of the total (hydr)oxide powder (calculated as metal in each case). The remainder to 100% by weight is oxygen for the compounds present in oxidic form. Such a catalyst does not in fact need to contain (hydr)oxides of the alkaline earth metals; preferably, however, it contains at least one (hydr)oxide of the alkaline earth metals. If a plurality of (hydr)oxides of the alkaline earth metals is used, each of said (hydr)oxides is preferably present in an amount which is not less than 20% by weight and not greater than 80% by weight of said total range of 0.2 to 5% by weight.

DETAILED DESCRIPTION OF THE INVENTION

Of the alkaline earth elements, magnesium, calcium, strontium and barium, preferably strontium and barium, are particularly suitable.

Powders of oxides or hydroxides of said elements are used to prepare the catalysts. Preference is given to oxide powders of said elements. Such powders are mechanically blended with one another in ratios such that the weight ratios specified above are established. The remainder making up to 100% by weight is always the proportion of oxygen, and all the percentages by weight are relative to the total weight of the oxidic, support-free molded body. The mixture of the powders is then compressed on tableting or pelleting machines at high pressure, in which process graphite and/or adhesives in amounts of 0.5 to 1% by weight, relative to the total weight of the powder to be compressed, may also be used to improve the adhesiveness of the powder. Examples of the shape of such compacts are tablets, spheres or cylindrical granules having dimensions of 1 to 10 mm, preferably 3 to 7 mm. To increase the external surface area, tableted molded bodies may also be provided with an axial perforation. Viewed macroscopically, such compressed molded bodies have a smooth surface. The compressed molded bodies have a high compressive strength on the molded-body surface. Thus, tablets or cylindrical granules have a compressive strength of 200 to 800 N/cm$^2$, preferably 250 to 600 N/cm$^2$ on the flat compressed surfaces if a planar pressure stamp is used, and tablets, spheres or cylindrical granules have a compressive strength on the curved compressed surfaces of 50 to 200 N (measured as force), preferably 80 to 140 N, if a knife-shaped pressure transducer is used. The internal surface area of the compressed molded bodies used is 30 to 200 m$^2$/g, preferably 80 to 160 m$^2$/g. The compressive strength of the support-free molded bodies can be determined in accordance with DIN 50 106. The internal surface is determined in accordance with F. M. Nelson and F. T. Eggertsen, Analyt. Chem. 30 (1958), pages 1387 to 1390 or in accordance with S. J. Gregg and K.S.W. Sing, Adsorption Surface Area and Porosity, Academic Press, London 1982, chapters 2 and 6.

With the aid of the use of the catalysts described in the process according to the invention, a mixture of isomeric isocamphyl-cyclohexanols, such as 2-hydroxy-1-(5-isocamphyl)cyclohexane, 3-hydroxy-1-(5-isocamphyl)-cyclohexane, 4-hydroxy-1-(5-isocamphyl)cyclohexane, is produced from the isocamphyl-gualacols or isocamphyl-phenols used. The temperature range for the process according to the invention is 140 to 280° C., preferably 180 to 260° C. A hydrogen pressure of 20 to 400 bar, preferably 20 to 350 bar, particularly preferably 100 to 300 bar is employed.

The process according to the invention can be carried out continuously in the free-flowing phase using the catalysts disposed in the fixed bed, at least ten times the molar amount of hydrogen per mole of starting material passing through the reactor during the course of the process. The hydrogenation reactors may be individual high-pressure steel or steel-alloy tubes which are entirely or partly filled with the molded bodies, in which connection the use of the support-free molded bodies on trays and in wire baskets or similar internals may also be useful in the case of fairly large tube cross sections. Furthermore, high-pressure tube bundles may also be used inside a conrunon jacket, the individual tubes again being entirely or partly filled with the catalyst molded bodies.

The compressed, carrier-free catalysts are reduced by hydrogen and thereby activated. In principle, this is possible simultaneously with the hydrogenation of the starting material used, but a fairly long running-in phase is necessary before the catalysts achieve their full activity and, consequently, the maximum possible space-time yield is reached. It is therefore advantageous to reduce the catalyst before loading with the starting material. This activating reduction with hydrogen is carried out in the temperature range from 180 to 280° C. and in the pressure range from 20 to 300 bar. In this process, the atmospheric oxygen initially present is first completely removed by an inert gas, such as nitrogen, argon, methane or ethane before a proportion of 10 to 15% by volume of hydrogen is added to the inert gas. Preferably, the inert gas is nitrogen for reasons of good availability. Within a specified time interval, for example of 24 hours, the proportion of inert gas is then continuously reduced and the inert gas is finally completely removed so that activation and reduction are carried out with pure hydrogen. The reduction is complete when the catalyst no longer consumes any hydrogen and, consequently, no longer forms any water of reaction.

In the free-flowing phase of the procedure, the weight hourly space velocity is 0.05 to 1.0 kg, preferably 0.1 to 0.5 kg of feedstock per liter of catalyst and per hour. The isocamphyl-guaiacols or isocamphyl-phenols used may be diluted with a suitable solvent which is inert to the reaction, for example aliphatic monoalcohols or cyclohexanol in an amount of 10 to 100, preferably 10 to 40% by weight, relative to the weight of the feedstock.

The catalysts used according to the invention have very high service lives; hitherto, 12,000 to 15,000 hours have been observed in which experiments were terminated without detectable reduction in the activity.

The reaction products obtained are virtually free of aromatic components. After the hydrogenation without solvent, the isocamphyl-cyclohexanols obtained can be processed further in a normal manner without a further purification process after distillative removal of any low boilers formed, and in the case of hydrogenation using a solvent they can be processed further after additionally distilling off the solvent. However, it is also possible to separate and concentrate the isocamphyl-cyclohexanols obtained distillatively or using other known physical methods of separation.

EXAMPLES

Example 1

A vertical-standing, thermally insulated high-pressure tube made of stainless, acid-resistant steel having an internal diameter of 45 mm and a length of 1 m which had been previously flushed with nitrogen so as to be oxygen-free, was filled with 1.4 l of molded bodies produced by tableting powders of cobalt, manganese and copper oxides. The cobalt content of the tablets was 54% by weight, the manganese content 15% by weight and the copper content 0.2% by weight. With a cylinder height of 5 mm and a diameter of 5 mm, the tablets had a compressive strength of 415 N/cm$^2$ on the planar cylinder surface and of 120 N on the curved molded body surface and also an internal surface area of 165 m$^2$/g.

The tablets were first dried for 6 hours in the nitrogen flow (temperature: 200° C. max., flow rate: 5 Nm$^3$N$_2$/h). The activation was carried out at a nitrogen pressure of 200 bar at a temperature between 180 and 280° C., hydrogen, whose mixing proportion was initially 10 to 15% by volume, being gradually added to the nitrogen. In the course of 24 hours, the nitrogen proportion in the gas mixture was increasingly reduced until pure hydrogen finally flowed through the reactor. The activation was stopped as soon as water of reaction no longer accumulated in the downstream trap.

After activation of the catalyst, the hydrogen pressure in the reactor system was increased to 300 bar. Then 170 g of a 38%-strength solution by weight of a mixture of isocamphyl-guaiacols, such as is produced in the alkylation of camphene with guaiacol, in cyclohexanol were pumped hourly together with 1.5 Nm$^3$ of hydrogen through the high-pressure tube from top to bottom at a pressure of 300 bar, the mixture to be hydrogenated being heated to a temperature of 190° C. in an upstream, electrically heated heat exchanger before entering the high-pressure tube.

The reaction product leaving the reaction tube was cooled in a second heat exchanger (water cooler) at 300 bar hydrogen pressure to a temperature of <60° C. and separated in a gas trap from excess hydrogen, which was fed back into the reaction system again.

After further cooling to a temperature of <30° C. and letting down the pressure to normal pressure, the reaction product was examined by UV spectroscopy.

It was found that the residual aromatic component was less than 0.1% by weight.

After distilling off the solvent, a glass-clear viscous oil was obtained which contained the isomeric isocamphyl compounds 2-hydroxy-1-(5-isocamphyl)-cyclohexane, 3-hydroxy-1-(5-isocamphyl)-cyclohexane and 4-hydroxy-1-(5-isocamphyl)-cyclohexane in a mixing ratio of approximately 3:1:2 and smelt pleasantly of sandalwood.

The catalyst had an unaltered activity after a service life of 10,106 hours.

Example 2

A vertical-standing, thermally insulated high-pressure tube made of stainless, acid-resistant steel having an internal diameter of 45 mm and a length of 1 m which had been previously flushed with nitrogen so as to be oxygen-free, was filled with 1.4 l of molded bodies produced by tableting powders of cobalt, manganese, barium and copper oxides. The cobalt content of the tablets was 53% by weight, the manganese content 14% by weight, the barium content 0.9% by weight and the copper content 0.2% by weight. With a cylinder height of 5 mm and a diameter of 5 mm, the tablets had a compressive strength of 420 N/cm$^2$ on the planar cylinder surface and of 128 N on the curved molded body surface and also an internal surface area of 168 m$^2$/g.

The tablets were first dried for 6 hours in the nitrogen flow (temperature: 200° C. max., flow rate: 5 Nm$^3$N$_2$/h). The activation was carried out at a nitrogen pressure of 200 bar at a temperature between 180 and 280° C., hydrogen, whose mixing proportion was initially 10 to 15% by volume, being gradually added to the nitrogen. In the course of 24 hours, the nitrogen proportion in the gas mixture was increasingly reduced until pure hydrogen finally flowed through the reactor. The activation was stopped as soon as water of reaction no longer accumulated in the downstream trap.

After activation of the catalyst, the hydrogen pressure in the reactor system was increased to 300 bar. Then 180 g of a 38%-strength solution by weight of a mixture of isocarnphyl-guaiacols, such as is produced in the alkylation of camphene with guaiacol, in cyclohexanol were pumped hourly together with 1.5 Nm$^3$ of hydrogen through the high-pressure tube from top to bottom at a pressure of 300 bar, the mixture to be hydrogenated being heated to a temperature of 210° C. in an upstream, electrically heated heat exchanger before entering the high-pressure tube.

The reaction product leaving the reaction tube was cooled in a second heat exchanger (water cooler) at 300 bar hydrogen pressure to a temperature of >60° C. and separated in a gas trap from excess hydrogen, which was fed back into the reaction system again.

After further cooling to a temperature of <30° C. and letting down the pressure to normal pressure, the reaction product was examined by UV spectroscopy.

It was found that the residual aromatic component was less than 0.1% by weight.

After distilling off the solvent, a glass-clear viscous oil was obtained which contained the isomeric isocamphyl compounds 2-hydroxy-1-(5-isocamphyl)-cyclohexane, 3-hydroxy-1-(5-isocamphyl)-cyclohexane and 4-hydroxy-1-(5-isocamphyl)-cyclohexane in a mixing ratio of approximately 3:1:3 and smelt pleasantly of sandalwood.

The catalyst had an unaltered activity after a service life of 4,026 hours.

What is claimed is:

1. A continuous process for preparing isocamphyl-cyclohexanols from isocamphy-guaiacol or isocamphyl-phenol compounds by hydrogenating one of said compounds with hydrogen at elevated temperature and elevated pressure, comprising the use of support-free molded bodies which serve as catalysts and which are obtainable by reduction of molded bodies made of compressed powders of cobalt, manganese and copper (hydr)oxides and optionally of (hydr)oxides of the alkaline earth metals.

2. The process as claimed in claim 1, characterized in that the molded bodies comprise (calculated as metal in each case) 40 to 65% by weight of cobalt, 10 to 20% by weight of manganese, 0.1 to 0.5% by weight of copper and 0 to 5% by weight of alkaline earth metal, the percentages relating to the total amount of metal oxide powder mixture.

3. The process as claimed in claim 1, characterized in that one or more (hydr)oxides of the alkaline earth metals may be present in the compressed (hydr)oxide powder, in which case, if a plurality of (hydr)oxide powders are present, each of said (hydr)oxide powders are present in an amount which is not less than 20% by weight and not greater than 80% by weight of the total content of up to 5% by weight.

4. The process as claimed in claim 1, characterized in that the molded bodies have a compressive strength of 300 to 800 N/cm$^2$ on the molded body surface.

5. The process as claimed in claim 1, according to which the molded bodies have an internal surface of 30 to 200 m$^2$/g.

6. The process as claimed in claim 1, according to which the hydrogen pressure is 20 to 400 bar.

7. The process as claimed in claim 1, according to which the hydrogenation temperature is 140 to 240° C.

8. The process as claimed in claim 1, characterized in that at least ten times the molar amount of hydrogen passes through the reactor per mole of starting material during the process.

9. The process as claimed in claim 1, characterized in that fixed catalysts are continuously employed in the free-flowing phase and a weight hourly space velocity of 0.05 to 1.0 kg, of starting product per liter of catalyst and per hour is established.

10. The process as claimed in claim 1, characterized in that the catalysts are reduced by treatment with hydrogen at 180 to 280° C. and 20 to 300 bar hydrogen pressure before they are used, the hydrogen being used as hydrogen/inert-gas mixture at the beginning of the reduction and the inert-gas component being removed completely in the course of the reduction.

11. The process as claimed in claim 1, characterized in that the feedstock is diluted with 10 to 100% by weight, of a solvent which is inert to the reaction, relative to the feedstock.

12. The process as claimed in claim 6, according to which the hydrogen pressure is 50 to 350 bar.

13. The process as claimed in claim 12, according to which the hydrogen pressure is 100 to 300 bar.

14. The process as claimed in claim 7, according to which the hydrogenation temperature is 160 to 230° C.

15. The process as claimed in claim 9, wherein said weight hourly space velocity of 0.1 to 0.5 kg of starting product per liter of catalyst and per hour is established.

16. The process as claimed in claim 11, wherein the feedstock is diluted with 10 to 40% by weight of a solvent which is inert to the reaction, relative to the feedstock.

* * * * *